United States Patent [19]

Sklar

[11] 4,124,381

[45] Nov. 7, 1978

[54] NON-PRECIOUS DENTAL CASTING ALLOY

[76] Inventor: Steven D. Sklar, 16 Cypress Ct., Brooklyn, N.Y. 11208

[21] Appl. No.: 718,763

[22] Filed: Aug. 30, 1976

[51] Int. Cl.$^2$ ............................................. C22C 19/05
[52] U.S. Cl. .................................................... 75/171
[58] Field of Search .................... 75/171, 170; 148/32, 148/32.5

[56] References Cited

U.S. PATENT DOCUMENTS

| | | | |
|---|---|---|---|
| 2,051,562 | 8/1936 | Lohr | 75/171 |
| 2,515,185 | 7/1950 | Bieber et al. | 75/171 |

*Primary Examiner*—R. Dean
*Attorney, Agent, or Firm*—Brumbaugh, Graves, Donohue & Raymond

[57] ABSTRACT

Non-precious dental casting alloys containing about 67-73% nickel, about 18-24% chromium, about 1.85-2.5% silicon, about 2.5-3.5% aluminum, about 0.4-2% titanium and about 2.5-5.5% iron, and preferably also about 0.002-1.50% zirconium. These alloys, due to a controlled silicon-chromium ratio of about 1:10 and the presence of titanium, and preferably also zirconium, are useful in making dental prosthetic applicances having improved strength, metal-ceramic bonding, and casting properties.

1 Claim, No Drawings

NON-PRECIOUS DENTAL CASTING ALLOY

This invention broadly relates to dental casting alloys, and more particularly, to non-precious dental casting alloys which are most suitable for forming denture prosthetic applicances having an improved metal-ceramic bond and improved overall strength and casting properties.

Nickel-chromium alloys containing silicon, aluminum and iron are known to provide a basis for the formation of suitable materials for making denture prosthetics. In many nickel-chromium alloys used for this purpose, boron is added as an aid in casting and to enhance the metal-ceramic bond. Molybdenum is sometimes added to improve bonding (metal-ceramic) and to prevent corrosion and caustic deterioration. Manganese also improves the bonding properties of nickel-chromium alloys used for dentures. More recently, beryllium is being used and has been found to provide satisfactory casting, soldering and bonding properties. However, none of these nickel-chromium alloys presently in use is capable of providing the improved metal-ceramic bond and overall strength and casting characteristics achieved with alloys of the present invention. The alloys according to the invention achieve the most desirable properties of both non-precious and precious dental metal materials.

According to the invention, dental casting alloys comprise about 67–73% nickel, about 18–24% chromium, about 1.85–2.5% silicon, about 2.5–3.5% aluminum, about 0.4–2% titanium, and about 2.5–5.5% iron, and preferably also about 0.002–1.50% zirconium. In the alloys of the invention, the weight ratio of silicon to chromium is about 1:10. These alloys have been found to provide prosthetic denture devices having greatly superior casting properties and which form a metal to porcelain bond of increased strength.

The improved properties of the nickel-chromium alloys according to the invention for making denture prosthetic appliances are based upon a highly controlled silicon-chromium ratio and the presence of titanium, and preferably also zirconium, in the alloy. The approximate 1:10 silicon-chromium ratio used in the invention is derived from the binary phase diagram for silicon and chromium. The ratio employed in the alloys according to the invention is based upon the eutectic point of the phase diagram at about 9% silicon and 91% chromium by weight. At this eutectic point, the melting point of the silicon-chromium alloy is approximately 300° F. lower than pure chromium and 120° F. lower than 86% chromium and 14% silicon. As the silicon-chromium ratio varies from the 9/91 ratio, the melting point of the binary alloy increases significantly. Accordingly, the use of the 9/91 ratio of silicon to chromium in the alloy according to the invention permits a most novel and beneficial application to denture prosthetic use. The "eutectic point" silicon-chromium ratio employed according to the invention permits the use of a "high percentage" chromium alloy for dentures without impairing strength or casting properties. Moreover, a higher percentage of chromium aids in preventing plaque build-up on the denture.

The titanium in the alloy according to the invention serves as the "bonding medium" between the alloy and the dental porcelain. Titanium above 1700° F. begins a diffusion process into the ceramic glassy material setting up a continuous network of "mechanical" bonds on the surface between the metal and ceramic. Titanium, due to its high affinity for oxygen, partially reduces the contact surface of the porcelain and thereby forms a compact oxide on the surface of the metal to further enhance the bond. Titanium is also added to prevent the depletion of the chromium as a carbide (chromium carbide) at grain boundries. Formation of titanium carbide prevents the formation of chromium carbide. Chromium carbide causes a deficiency of chromium at grain boundaries thereby making the alloy more susceptible to intergranular corrosion.

Zirconium is present in the most preferred alloys according to the inventionn. Zirconium when added to the alloys in quantities specified affects the grain boundry activity during casting. Zirconium acts as a grain refiner and reduces the grain size, tightening up the grain structure and increasing the elongation and ductility of the alloy. As such, the alloys according to the invention with zirconium undergo a greater amount of deformation before fracture is reached. As a dental alloy, this would enable an office practitioner to make minor chairside adjustments for a patient as required, without having to return the prosthetic applicance to the dental laboratory. This is, of course, a great advantage over previous nickel-chromium alloys which are much stiffer and harder, making dental chairside adjustments at best impractical.

Zirconium also plays a role very similar to that of titanium as an additional "bonding medium" between the metal and ceramic. However, titanium is essential to the alloys of the invention since zirconium is more reactive to oxygen. Because of its higher oxygen affinity, zirconium can only be present in the alloy in amounts less than approximately 1.5% since above that amount it would be impossible to prevent heavy zirconium oxidation and other undersirable side effects in the melting process.

The aluminum in the alloy provides oxidation resistance at elevated temperatures in both the casting of the alloy and in the application of the dental ceramic material, i.e., porcelain. It also provides a protective cover for the titanium and zirconium in the alloy. When the alloy is melted, the aluminum protects the titanium, and zirconium in amouts less than 1.5% by weight, by forming a very stable oxide (aluminum oxide) skin or shell around these elements which prevents any further oxidation.

The excellent properties of the alloys according to the invention make them similar in many desirable ways to the more expensive precious metals, while providing greater strength. Where precious metals are used in forming denture prosthetics, the wall thickness of the metal understructure to receive the porcelain must be no thinner than about 0.5 mm since normal fabrication procedures would cause any thinner metal to be greatly compressed and to flex which usually results in fracture of the porcelain jacket. On the other hand, the non-precious metal alloys according to the invention can be safely brought down to a thickness of 0.1 mm without risk of porcelain fracture.

Seven alloys according to the invention were prepared in the weight proportions set forth below in Table A.

TABLE A

|          | I     | II    | III   | IV    | V     | VI    | VII   |
|----------|-------|-------|-------|-------|-------|-------|-------|
| Nickel   | 67.00 | 67.00 | 67.10 | 70.25 | 71.60 | 71.32 | 67.00 |
| Chromium | 22.15 | 23.00 | 23.75 | 19.30 | 19.61 | 17.00 | 23.00 |
| Silicon  | 2.19  | 2.275 | 2.349 | 1.90  | 1.938 | 1.68  | 2.275 |
| Aluminum | 3.00  | 3.00  | 3.50  | 3.00  | 3.00  | 3.50  | 3.125 |

TABLE A-continued

|  | I | II | III | IV | V | VI | VII |
|---|---|---|---|---|---|---|---|
| Titanium | 1.10 | 1.10 | 0.60 | 1.10 | 1.20 | 1.50 | 0.40 |
| Iron | 4.54 | 3.60 | 2.501 | 4.42 | 2.65 | 5.00 | 3.00 |
| Zirconium | 0.02 | 0.025 | 0.20 | 0.03 | 0.002 | — | 1.00 |

The alloys prepared as set forth in Table A above were tested for overall strength, casting properties and boundability to porcelain. All seven of the alloys set forth in Table A were tested for strength by measuring their ultimate tensile strength and elongation. In addition, yield strength tests were performed on alloys II, V, VI and VII where average values of about 80,000–85,000 psi were recorded.

An Instron universal testing instrument was used to measure the ultimate tensile strength (U.T.S.) and elongation of the alloys. All samples as test rods were physically attached to the load cell by grips with special jaws to hold the samples without damaging them for tension testing. All test rods were cast by the lost wax technique (centrifical casting) which is the same technique used in fabrication of dental prosthesis. The test specimens were approximately 3 inches long with a diameter of about 0.075 inches. Tensile forces were applied by a moving crosshead operated by two vertical lead screws. The load weighing system recorded tensile load in pounds on a strip chart recorder. Samples were tested at a crosshead speed of 0.2 inches/minute.

The amount of elongation, which was measured over a two inch length, was determined by fitting the broken rod pieces together and measuring the amount of stretch in the broken specimen.

The yield strength was measured by the use of an extensiometer. The amount of stress every 0.01 inches of extension of material was recorded. The yield strength was then calculated by a standard 2% offset technique.

All sample rods were tested in two different test conditions. The samples were either cast and allowed to air cool to room temperature and tested with no further heat treatments, or subjected to a further dental heat treatment (D.H.T.). The D.H.T. samples were cast, allowed to air cool to room temperature and then processed through a porcelain firing cycle, which simulates the dental lab processing of the prosthesis. More particularly, the D.H.T. used was a three-step process whereby a sample at 1200° F. is heated under vacuum to 1800° F. and then further heated in air to 1850° F. with subsequent air cooling. This step is repeated and then the sample at 1200° F. is again heated under vacuum to 1700° F. and then further heated in air to 1750° F. with final air cooling. The rate of heating during all three heating steps is 90° F. per minute.

Table B below is a summary of ultimate tensile and yield strengths, and elongations of the alloys tested in the two conditions. Each reported result is an average of a minimum of 10 samples, except for the yield strength values which are based upon a two-sample test.

TABLE B

|  | Air cooled | | | Air cooled & D.H.T. | | |
|---|---|---|---|---|---|---|
|  | Yield Strength (psi) | U.T.S. (psi) | % Elongation | Yield Strength (psi) | U.T.S. (psi) | % Elongation |
| Alloy No. I |  | 117,400 | 4 |  | 118,100 | 5 |
| II | 80,400 | 119,700 | 4 | 80,900 | 120,950 | 4 |
| III |  | 121,000 | 7 |  | 124,500 | 7 |
| IV |  | 126,330 | 5 |  | 121,500 | 6 |
| V | 80,150 | 127,600 | 4 | 81,500 | 130,750 | 4 |
| VI | 84,000 | 133,000 | 1.5 | 84,000 | 135,500 | 2 |
| VII |  | 121,650 | 4 | 85,650 | 118,300 | 3 |

All seven samples were tested for bondability to porcelain according to standard bond-shear tests as follows:

Metal rods approximately 3 inches in length with a diameter of about 0.083 inches were cast and used for fabricating bond test specimens.

Specimens were prepared by placing a three inch rod into a drilled (cored) aluminum cylinder 2½ inches high and 1 inch in diameter. The drilled hole was approximately 0.086 inches allowing just enough room for the rod to fit into the opening. An aluminum washer with dimensions of 0.080 inches thick, with an outside diameter of 1 inch and an inside diameter 0.500 inches, was used as a temporary mold to shape the dental porcelain disc around the test rod. The test specimen was now carefully removed from the aluminum mold and allowed to dry slowly in front of a furnace muffle set at about 1000° F. and then processed through the standard dental porcelain cycle under a vacuum. The dental porcelain cycle comprises heating a sample at 1200° F. to 1800° F. under a vacuum, releasing the vacuum and continuing heating to 1850° F. in air thereafter removing the sample immediately and placing it under a pyrex beaker. Repeat this for a second time, then heat specimen from 1200° F. to 1700° F. under vacuum, release vacuum and continue to heat in air to 1750° F., remove immediately and place under a pyrex beaker. All heating was done at 90° F. per minute.

After the test specimens had cooled, the rod was coated with silicone greased approximately ¼ inch on both sides of the fired porcelain disc. Then the porcelain end of the test specimen was embedded in dental stone approximately three-fourths of an inch in diameter and three-fourths of an inch in length. This allowed the test specimen to be handled and loaded (or tested) more efficiently.

The specimens were tested in a universal tensile testing machine at a crosshead speed of 0.020 inches/minute. Four samples for each alloy were tested. The average porcelain disc was about 0.075 inches thick. The bond strength was reported in pounds per square inch (psi), the load in pounds, and the contact surface area in square inches.

Table C below represents the results of the porcelain bond or bond-shear tests:

TABLE C

| Alloy No. | Number of Test | Contact Surface Area (inches) | Load (pounds) | Bond Strength (psi) | Avg. Bond Strength |
|---|---|---|---|---|---|
| I | 1 | 0.01956 | 275 | 14,059 | |
| | 2 | 0.02032 | 281 | 13,829 | |
| | 3 | 0.01926 | 269 | 13,967 | |
| | 4 | 0.01825 | 254 | 13,918 | 13,943 |
| II | 1 | 0.01956 | 279 | 14,264 | |
| | 2 | 0.02032 | 272 | 13,386 | |
| | 3 | 0.01877 | 257 | 13,692 | |
| | 4 | 0.01903 | 270 | 14,188 | 13,882 |
| III | 1 | 0.01976 | 250 | 12,652 | |
| | 2 | 0.01929 | 241 | 12,493 | |
| | 3 | 0.01956 | 253 | 12,934 | |
| | 4 | 0.01851 | 237 | 12,804 | 12,721 |
| IV | 1 | 0.01999 | 285 | 14,257 | |
| | 2 | 0.01929 | 277 | 14,360 | |
| | 3 | 0.01949 | 269 | 13,802 | |
| | 4 | 0.01838 | 268 | 14,581 | 14,250 |
| V | 1 | 0.02034 | 297 | 14,602 | |
| | 2 | 0.01982 | 300 | 15,136 | |
| | 3 | 0.01979 | 284 | 14,350 | |
| | 4 | 0.01982 | 295 | 14,884 | 14,743 |
| VI | 1 | 0.01956 | 301 | 15,388 | |
| | 2 | 0.01932 | 308 | 15,942 | |
| | 3 | 0.01829 | 287 | 15,691 | |
| | 4 | 0.01929 | 311 | 16,122 | 15,786 |
| VII | 1 | 0.01982 | 250 | 12,613 | |
| | 2 | 0.01958 | 241 | 12,308 | |
| | 3 | 0.01932 | 237 | 12,267 | |
| | 4 | 0.01982 | 248 | 12,513 | 12,425 |
| | | square inches | pounds | pounds/ square inch (psi) | psi |

Casting properties were tested by comparing the seven alloy samples to a pure gold sample and a white gold dental alloy containing 62 parts gold with a balance of palladium, silver and indium. The method of casting used was the lost wax, centrificial casting technique.

Two sets of wax strips were invested. In the first set, the size of the wax strips were 6 mm in width, 50 mm in length and 0.3 mm in thickness. In the second set, the wax strips were 6 mm in width, 50 mm in length and 0.1 mm in thickness. In the first set, there were no miscasts. In the second set, the pure gold and the seven alloys of invention casted completely with no voids. The white gold sample, however, did not cast completely with sections of this thin casting that were completely miscast (unfilled).

These casting tests indicate that the fine casting characteristics of the seven invention alloys, when compared to the pure gold and white dental gold samples, have superior casting properties over the white dental gold alloy containing 62 parts gold.

To demonstrate the value of the zirconium in the preferred embodiments, alloy V in Table A above was compared with a similar alloy without zirconium in which the percentage of nickel was increased to 71.602%. The results of elongation tests show that the alloy V had an elongation of approximately 4%, while the experimental alloy without zirconium had an elongation of only approximately 1.5%. A similar test was conducted to compare alloy III from Table A with a similar alloy containing no zirconium and a correspondingly increased amount of nickel. Thest test results show that alloy III had a elongation of approximately 7% while the corresponding experimental alloy without zirconium had a substantially decreased elongation of approximately 2%.

It should be understood that, although particular embodiments of this invention have been described in the foregoing specification in detail by way of illustration, this invention includes all modifications and equivalents there of which fall within the scope of the appended claims.

I claim:

1. A non-precious dental casting alloy consisting essentially of about 67–73% nickel, about 18–24% chromium about 1.85–2.5% silicon, about 2.5–3.5% aluminum, about 0.4–2% titanium, about 2.5–5.5% iron, and about 0.002–1.5% zirconium, wherein the ratio of silicon-chromium is about 1:10.

* * * * *